United States Patent [19]

Schnaper et al.

[11] Patent Number: 4,665,021

[45] Date of Patent: May 12, 1987

[54] DIAGNOSTIC METHOD OF SCREENING FOR IMMUNE DEFICIENCY IN A NEPHROTIC PATIENT BY DETERMINATION OF SIRS IN THE URINE

[76] Inventors: H. William Schnaper, 12952 Mayerling Dr., Creve Coeur, Mo. 63146; Thomas M. Aune, 650 E. Adams, Kirkwood, Mo. 63122

[21] Appl. No.: 653,123

[22] Filed: Sep. 21, 1984

[51] Int. Cl.$^4$ .................. G01N 33/53; G01N 33/20; G01N 33/566; C12P 21/00
[52] U.S. Cl. .................................. 435/7; 435/68; 435/803; 436/74; 436/161; 436/528; 436/817; 436/501; 530/351
[58] Field of Search ................. 435/7, 803, 68; 436/501, 815, 817, 74, 161, 528; 530/351

[56] References Cited

PUBLICATIONS

Rich and Pierce, *J. Immunol.*, 112, 1360–1368, (1974).

Aune and Pierce, *Proc. Natl. Acad. Sci. USA*, 79, 3808–3812, (1982).
Aune and Pierce, *Lymphokines*, vol. 9, E. Peck (ed), Academic Press Inc., New York, 1984, pp. 257–277.
Schnaper, Pierce and Aune, *J. Immunol*, 132, 2429–2435, (1984).
Aune, Webb and Pierce, *J. Immunol.*, 131, 2848–2852, (1983).
Schnaper and Aune, *Fed. Proc.*, 43, Abst. 2911, Mar. 1984.
Schnaper and Aune, *Ped. Res.*, 18, Abst. 1637, May 1984.

*Primary Examiner*—Christine M. Nucker
*Assistant Examiner*—Patricia DeSantis
*Attorney, Agent, or Firm*—Scott J. Meyer; James W. Williams, Jr.

[57] ABSTRACT

The disclosure relates to an in vitro diagnostic method of screening for immune deficiency in a nephrotic patient comprising administering the presence or absence of the lymphokine, soluble immune response suppressor, in a urine sample of said patient.

4 Claims, 3 Drawing Figures

DIAGNOSTIC METHOD OF SCREENING FOR IMMUNE DEFICIENCY IN A NEPHROTIC PATIENT BY DETERMINATION OF SIRS IN THE URINE

BACKGROUND OF THE INVENTION

This invention relates to a medical diagnostic method and, more particularly, to an in vitro diagnostic method of screening for immune deficiency in nephrotic patients.

The nephrotic syndrome (NS) is characterized by extensive urinary loss of albumin leading to hypoalbuminemia, edema and hypercholesterolemia. See, for example, Brenner and Stein, *Contemporary Issues in Nephrology*, Vol. 9, Nephrotic Syndrome, Churchill Livingston, New York, 1982, pp. 1–308. Patients with this syndrome frequently have suppressed clinical and in vitro immune responsiveness; the disease in which this Ohenomenon has been most extensively studied is minimal change nephrotic syndrome (MCNS). Unique attributes of MCNS include the lack of morphological changes sufficient to account for proteinuria, the observed pattern of glomerular permselectivity, a frequent association with antecedent immunogenic stimuli, and the marked responsiveness of this disease to immunomodulatory agents. Patients with MCNS show evidence of decreased cellular immunity. Furthermore, their sera have been found to suppress lymphocyte proliferation and to show cytotoxic activity. Enhanced suppressor cell function has also been described. Thus, clinical evidence of altered immunity appears to be associated with increased suppressor cell activity.

Patients with nephrotic syndrome frequently have suppressed immune responsiveness by both clinical and in vitro evaluation. Thus, bacterial infection, particularly primary peritonitis, frequently occurs during relapse. MCNS patients also have decreased skin reactivity to tuberculin and dinitrochlorobenzene which improves with remission of symptoms. Elevated percentages of both T and B lymphocytes have been demonstrated by techniques of examining either rosetting or cell surface marker expression. In addition, serum immunoglobulin levels are abnormal, with relapse-associated increased IgM and decreased IgG levels being reported in MCNS and other forms of nephrotic syndrome as well. Specific titers may also be affected, since a patient has been reported to show an appropriate initial response to pneumococcal polysaccharide vaccine but a subsequent rapid decrease in titer.

More recently, immune responses in nephrotics have been evaluated using in vitro techniques. Patient sera have been found to be toxic to control lymphocytes; increased serum migration inhibitory factor activity, and increased monocyte cytotoxicity against cultured renal epithelial cells have also been described. Several studies have shown decreased lymphocyte proliferation in the presence of sera from MCNS patients in relapse. A heat-stable substance in patient serum has been described which binds to normal lymphocytes and decreases the proliferative response to mitogens. Increased Concanavalin A-activated suppressor cell activity has also been reported in MCNS patients in relapse compared to healthy controls, patients in remission, and patients with glomerulonephritis. Although these findings appear most striking in MCNS, they may not be restricted to minimal change disease; several of the studies mentioned above found similar abnormalities in other forms of nephrotic syndrome.

Despite this considerable body of information, the mechanism of immune suppressive activity is unclear. Although the basic mechanism of suppressed responses in MCNS remains unclear, suppressor cells have been shown in most basic systems to act through release of soluble suppressor factors. One such system which has been fairly well-characterized is the soluble immune response suppressor (SIRS) pathway. SIRS is a product of mitogen- or interferon-activated murine or human suppressor T lymphocytes which inhibits in vitro production of antibody when added at or near initiation of lymphocyte cultures. See, for example, Rich and Pierce, *J. Immunol.* 112, 1360–68 (1974); and Aune and Pierce, *Proc. Natl. Acad. Sci. USA* 79, 3808–12 (1982). Suppression also occurs when factor is added late in the culture period after activation to its suppressive form, $SIRS_{ox}$, by reaction with low concentrations of $H_2O_2$, as described by Aune and Pierce, *Lymphokines*, Vol. 9, E. Pick (ed), Academic Press Inc., New York, 1984, pp. 257–77. Human SIRS has a molecular weight of 110–150,000 daltons when fractionated by chromatography on Sephracryl ®-200 gel using buffers of physiologic ionic strength and 10–15,000 daltons when eluted in high ionic strength buffers. It is acid and protease sensitive, and its in vitro activity is blocked by levamisole and catalase, which block activation of SIRS to $SIRS_{ox}$, and by 2-mercaptoethanol (2-ME), which inactivates $SIRS_{ox}$. Such characterization of human SIRS is disclosed by Schnaper, Pierce and Aune, *J. Immunol.* 132, 2429–35 (1984). Inhibition of suppression by these reagents and activation by peroxide are characteristic of both murine and human SIRS and are useful techniques in screening for the presence of SIRS in other systems. For further background information on the purification and characterization of SIRS, see also Aune, Webb and Pierce, *J. Immunol.* 131, 2848–52 (1983).

In view of the foregoing, it is believed that it would be useful to be able to relate immune suppression to disease etiology and that a diagnostic method of screening for immune deficiency in nephrotic patients would be of considerable importance to establish such relation.

BRIEF DESCRIPTION OF THE INVENTION

This invention relates to an in vitro diagnostic method of screening for immune deficiency in a nephrotic patient comprising determining the presence or absence of the lymphokine, soluble immune response suppressor (SIRS), in a urine sample of said patient.

The presence or absence of SIRS in a urine sample can be determined by comparing the urine sample with a control sample known to contain SIRS, or by analyzing the urine sample for constituent protein having the physical, chemical or functional characteristics of SIRS. Illustratively, suppressive activity in the urine of nephrotic patients is identified as human SIRS by various functional and physical criteria such as: (1) molecular weight estimated by gel filtration; (2) kinetics of suppression; (3) inhibition of suppression by treatment with catalase, levamisole, or 2-mercaptoethanol; (4) abrogation of activity by treatment with acid or protease; (5) elution pattern on high performance liquid chromatography; and (6) cross-reactivity with monoclonal anti-murine SIRS antibodies.

Surprisingly, only a distinct population of patients, those who had nephrotic syndrome from diseases classically associated with an immune pathogenesis, excreted SIRS.

The diagnostic method of this invention also can be used as an aid in the prediction of steroid-responsiveness of nephrotic syndrome.

Once steroid treatment has begun, repeat testing in patients who are slow to respond but previously showed urinary SIRS excretion may give an advance indication that response will occur shortly if SIRS has disappeared from the urine.

The diagnostic method of this invention also can be used to differentiate minimal change disease from focal sclerosis which would be useful since the prognosis is good in the former and poor in the latter situation.

The discovery of the presence of SIRS in the urine of nephrotic patients also enables the production of purified SIRS from urine by various protein isolation procedures.

DETAILED DESCRIPTION OF THE INVENTION

While the specification concludes with claims particularly pointing out and distinctly claiming the subject matter regarded as forming the present invention, it is believed that the invention will be better understood from the following description taken in conjunction with the accompanying drawings in which:

The following detailed examples will further illustrate the invention although it will be understood that the invention is not limited to these specific illustrative examples.

In these examples, the following methods were employed:

Patient population. Patients studied in these examples were under care of the Renal Division of St. Louis Children's Hospital and the Department of Pediatrics, Washington University School of Medicine. Urine samples were collected from patients who were evaluated for proteinuria. Diagnosis was made using established criteria of clinical presentation, serum chemistries, radiography, and where appropriate, renal biopsy. These criteria are described by Brenner and Stein (eds.), *Contemporary Issues in Nephrology*, Vol. 9, Nephrotic Syndrome, Churchill Livingston, New York, 1982, pp. 1–308; Grupe, *Postgrad. Med.* 65, 229–36 (1979). In many of the nephrotic children, the following criteria indicated a diagnosis of "steroid-responsive nephrotic syndrome" (SRNS): (1) normal serum complement activity, (2) no clinical or serologic evidence of collagen-vascular disease, (3) relatively benign urine sediment and (4) good response to steroid therapy. In these patients biopsy was deferred. All subjects were 2–18 years of age.

Collection and treatment of urine samples. Timed collections of urine (usually for 12 hours) were obtained from patients and maintained briefly at 4° C. until processing. Urines were concentrated, if necessary, by ultrafiltration to a volume less than about 200 ml, and preferably to a volume of about 150 ml using an Amicon ® DC-2 concentrator (Amicon, Danvers, MA), dialyzed against 40 volumes distilled water using either the Amicon DC-2 or 3500 Mol. Wt.-cutoff cellulose dialysis tubing (Spectrum Medical Industries, Los Angeles, CA), lyophilized and stored at −20° C. until use. Addition of protease inhibitors prior to processing did not affect activity in the earliest samples collected and was thus omitted thereafter. Lyophilized specimens contained over 90 percent protein by weight, as determined by the method of Lowry et al.

Assay for antibody production. Human spleen cells were obtained aseptically from cadaver kidney transplant donors at the time of organ harvest, processed as described previously by Schnaper, Pierce and Aune, *J. Immunol.* 132, 2429–35 (1984), and preserved frozen in liquid nitrogen until use. Alternatively, human peripheral blood mononuclear cells (PBMC) were obtained from healthy volunteers and isolated by centrifugation over ficoll-sodium diatrizoate according to the method of Boyum, *Scand. J. Clin. Lab. Invest.* (*Suppl.*) 97, 77–89 (1968). Spleen cells ($1 \times 10^6$) or PBMC ($2 \times 10^6$) were suspended in 1 ml sterile RPMI 1640 medium (K.C. Biologicals, Kansas City, MO) supplemented with glutamine, penicillin/streptomycin, nonessential amino acids, and 10 percent fetal calf serum (FCS, Reheis Lots No. 58101 and 100361). Cells were cultured with pokeweed mitogen (PWM) at 6 μg/ml for 7 days in a 37° C., 5 percent $CO_2$, humidified atmosphere. After washing with Hank's balanced salt solution, the cells were resuspended in L-15 medium (Washington University School of Medicine Cancer Center) supplemented with 3 percent FCS and penicillin/streptomycin. Assay for antibody production employed a slide modification of the Jerne hemolytic plaque forming cell (PFC) assay as described by Schnaper, Aune and Pierce, *J. Immunol.* 131, 2301–06 (1983). A measured aliquot of cells was suspended in agarose with rabbit anti-human IgM antiserum (Boehringer-Mannheim, Indianapolis, IN) and sheep erythrocytes (SRBC) coated with staphyloccal protein A by the chromium chloride method of Sweet and Welborn, *J. Immunol.* 106, 1407-10 (1971). The mixture was allowed to gel on a glass slide. After a 4-hour incubation at 37° C., the slides were flooded with guinea-pig complement (Rockland; Gilbertsville, PA) causing plaques of hemolysis to form around antibody-producing cells. The number of plaques per slide, and hence the number of PFC per culture, was determined by using dark-field illumination and a binocular dissecting microscope.

Sample preparation. Because the concentration of protein in nephrotic urine is subject to marked variation, samples of urine from various patients were standardized according to a specific duration of excretion when resuspended in unsupplemented RPMI 1640 medium. During preliminary tests it was determined that optimal results were obtained when the amount excreted in 0.01 hours was resuspended in 1 ml of media. This usually represented about 1 mg/ml, with a range of 0.5 to 5 mg/ml. Resuspended urine samples were filter-sterilized (Gelman, Ann Arbor, MI) before addition to culture. Control responses were determined by the number of PFC/culture when PWM alone was added to cultures. Background PFC responses, assessed in cultures without PWM, amounted to less than 10 percent of PWM-stimulated culture responses and were not subtracted from these responses. In screening for suppressive activity, a titration curve was generated for each resuspended urine and the volume required to cause 50 percent suppression of control responses (one $S_{50}$ unit) determined graphically. Urine samples in which no suppressive activity was detected were retested over a broader titration range.

Fractionation of resuspended urines. One ml of urine was fractionated by gel filtration on a 1.75×28 cm (67.3 cm$^3$) column of Sephacryl ® S-200 (Sigma, St. Louis, Mo.) in phosphate-buffered saline (PBS) or 0.4M pyridine/0.4M acetic acid. Sephacryl is prepared by covalently cross-linking allyl dextran with N,N'-methylene bisacrylamide. The column was calibrated using aldolase (158,000 daltons), bovine serum albumin (BSA) (68,000 daltons) chymotrypsinogen A (25,000 daltons) and cytochrome C (13,000 daltons). Fractions of 2-ml were collected. Those eluted with pyridine-acetic acid were lyophilized and resuspended in PBS, and all fractions were filter-sterilized before testing in cultures. Fractions containing suppressive activity were pooled for use in subsequent tests.

Further background information on gel filtration chromatography can be had by reference to *Gel Filtration Theory and Practice*, Pharmacia Fine Chemicals AB, Uppsala, Sweden, 1979.

Reverse phase high performance liquid chromatography (HPLC) was performed by suspending lyophilized urine in 1.0M pyridine/0.5M acetic acid, pH 5.5 buffer. After clearing of particulate matter by centrifugation for 2 min. in a Beckman (Palo Alto, CA) microfuge, the solution was applied to a Lichrosorb ® RP-8 (10 µM, E. Merck, Darmstadt, FRG) column (250×4 mm) equilibrated in the same pyridine-acetic acid buffer. Protein was eluted with an increasing gradient of n-propanol. Fractions from HPLC were lyophilized and resuspended in PBS or culture medium before testing for SIRS bioactivity. Protein content of the fractions was measured by the method of Lowry with bovine serum used as a standard.

Further background information on HPLC can be had by reference to Hearn, "High Performance Liquid Chromatography and its Application to Protein Chemistry," *Advances in Chromatography*, Vol. 20, (Ed. J. Calvin Giddings et al.) Marcel Dekker, Inc., New York, 1982, Chapter 1, pp. 1-82.

Absorption of immunosuppressive activity using monoclonal anti-murine SIRS antibodies. Monoclonal anti-murine SIRS antibodies were obtained as follows: Partially purified murine SIRS ($5 \times 10^5$ units) in complete Freund's adjuvant was injected into Sprague-Dawley rats at biweekly intervals. Serum from each rat was bound to CNBr-activated agarose, Sepharose ® 6B (Sigma, St. Louis, MO), and the coupled beads were tested for ability to absorb murine SIRS activity from a standard solution ($10^3$ units/ml). Spleen cells from a rat demonstrating high serum anti-SIRS activity were fused to the myeloma cell line SP 2/0 and supernates from hybridoma wells tested for ability to absorb murine SIRS activity as described above. Four hybridomas producing anti-murine SIRS antibody were cloned. Each monoclonal antibody was coupled to CNBr-activated Sepharose 6B. A suspension of urine showing suppressive activity was incubated with the beads for one hour at 4° C. After centrifugation to remove the beads, the unbound material was tested for SIRS activity.

In general, monoclonal antibody production can be carried out by conventional procedure such as described, for example, by Köhler and Milstein, *Nature* 256, 495-7 (1975); *Eur. J. Immunol.* 6, 511-9 (1976). According to this method, tissue-culture adapted mouse myeloma cells are fused to spleen cells from immunized mice to obtain the hybrid cells that produce large amounts of a single antibody molecule. Purified SIRS is used as the immunogen by producing the desired anti-SIRS activity in accordance with the present invention. A suitable mouse myeloma cell line is the well-known SP2/0-Ag 14 cell line of BALB/c origin defined by Schulman et al., *Nature* 276, 269-70 (1978), the disclosure of which is incorporated herein by reference. Samples of these cells are available to the public from the American Type Culture Collection, Rockville, Md., under the accession number ATCC CRL-1581. A suitable method of carrying out the fusion of the myeloma cells and the immunized spleen cells is the conventional procedure described by Galfre et al., *Nature* 266, 550-2 (1977), whereby polyethylene glycol (PEG) is used as the fusing agent for the cells growing as monolayers. Cells can be cultured in HAT (hypoxanthine, aminopterin and thymidine) selection medium described by Littlefield, *Science* 145, 709 (1964).

For use of the monoclonal antibodies in the affinity chromatography for absorption of the immunosuppressive activity, they are preferably immobilized by the cyanogen bromide coupling method of Axen et al., *Nature* 214, 1302-4 (1967) and March et al., *Anal. Biochem.* 60, 149-52 (1974). For this procedure, pre-activated agarose is available as a stable lyophilized powder (CNBr-activated Sepharose 6B; Pharmacia Fine Chemicals, Uppsala, Sweden).

Further background information on the preparation and use of monoclonal antibodies can be had by reference to a general text such as, for example, Goding, *Monoclonal Antibodies: Principles and Practice*, Academic Press Inc., New York, 1983.

In these examples, urine samples from children with MCNS in relapse and other proteinuric renal diseases were tested for suppressive activity. Urine samples from all patients with MCNS and certain other nephrotic patients suppressed in vitro antibody-producing responses (see Example 1). This immunosuppressive activity was identical to human SIRS by the following criteria: (1) molecular weight estimated by gel filtration (see Example 2); (2) requirement for early addition to culture (see Example 3, Table 2); (3) activation by peroxide (see Example 3, Table 2); (4) inhibition of suppressive activity by catalase, levamisole or 2-mercaptoethanol (see Example 3, Table 3); (5) abrogation of activity by acid or protease treatment (see Example 3, Table 4); (6) elution pattern of high performance liquid chromatography (see Example 4); and cross-reactivity with monoclonal anti-murine SIRS antibody (see Example 5).

The relationship of urine SIRS activity to the disease state and steroid treatment of nephrotic syndrome was followed in several patients (see Example 6). The screening of urine samples from patients with various proteinuric renal disorders for suppressive activity on PFC cultures was carried out (see Example 7).

EXAMPLE 1

Suppression of PFC response by urines from patients with MCNS. Resuspended urine samples from four patients with MCNS were assayed for suppressive activity by adding graded amounts to pokeweed mitogen-stimulated lymphocytes 24 hours after culture initiation. PFC responses were determined on day 7. Table 1, below, shows results of an illustrative test. Addition of urine from a healthy volunteer (control sample) to which human serum albumin (1 mg/ml) had been added before processing did not significantly affect responses. However, 50 µl of urine from the four patients with MCNS, corresponding to 5 percent of culture volume, suppressed responses by over 70 percent. Although the degree of suppression and the dose of urine required to cause suppression varied among patients, suppressive activity was consistently observed in urines from these and similar patients.

TABLE 1

Inhibition of plaque forming cell (PFC) responses by nephrotic urine*

| µl Added | \multicolumn{4}{c}{PFC/Culture} | | | |
|---|---|---|---|---|
| | 0 | 20 | 50 | 200 |
| Control** | 5,600 | 6,300 | 5,600 | 5,980 |
| Patient 1 | — | 4,100 | 1,210 | 710 |
| Patient 2 | — | 1,420 | 1,400 | 1,360 |
| Patient 3 | — | 2,820 | 1,450 | 260 |
| Patient 4 | — | 3,650 | 1,380 | 2,060 |

*Urine samples from nephrotic patients were dialyzed and lyophilized, then resuspended in media. Aliquots were added to pokeweed mitogen-stimulated lymphocytes 24 hours after culture initiation. Polyclonal antibody production was determined 6 days later by the "reverse" PFC method using the Jerne hemolytic plaque forming cell assay.
**Albumin was added to the control urine sample which was obtained from a normal volunteer. In other experiments, presence or absence of albumin in the control urine did not affect responses.

EXAMPLE 2

Figure 1:
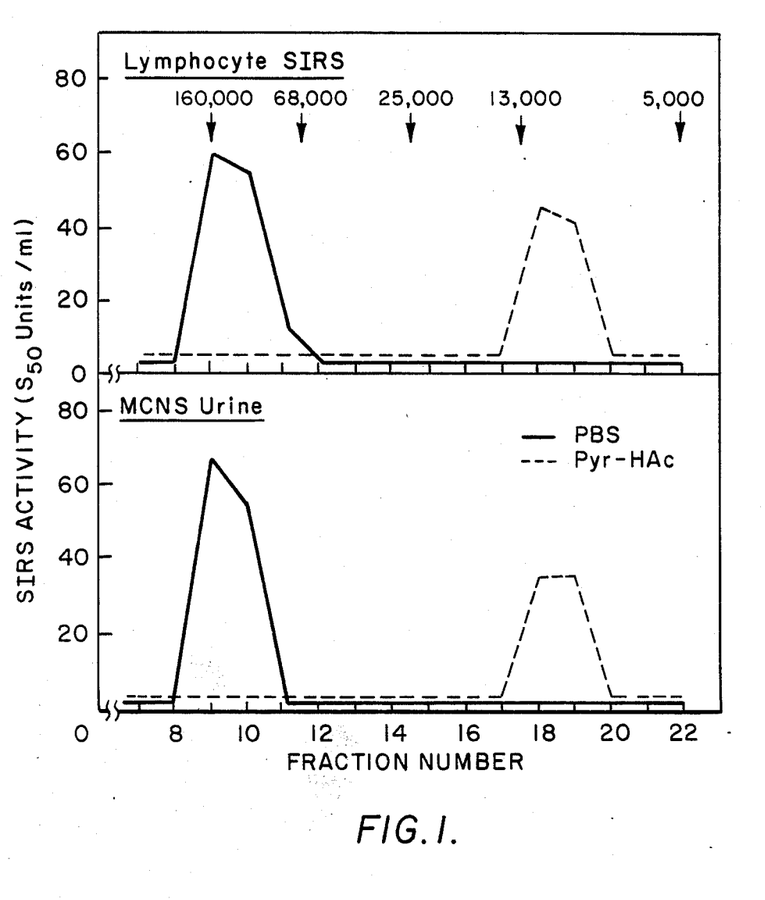
FIG. 1 shows the elution profiles from the fractionation of (a) lymphocyte-derived SIRS (soluble immune response suppressor) and (b) a urine sample of a patient with MCNS (minimal change nephrotic syndrome) by gel filtration chromatography with Sephacryl ® S-200. One ml of reconstituted urine was fractionated in either phosphate-buffered saline (solid line) or pyridine-acetic acid (broken line) and 2 ml fractions were collected. The upper graph shows a typical chromatographic pattern of lymphocyte SIRS activity. The lower graph shows that urine suppressive activity migrates identically. The column was calibrated using aldolase, bovine serum albumin, chymotrypsinogen A and cytochrome C.

Molecular weight of suppressor substance. To approximate the size of the suppressive moiety, urine with known suppressive activity was fractionated by gel filtration using Sephacryl S-200 chromatography. FIG. 1 of the accompanying drawings shows the results of experiments with both human, lymphocyte-derived SIRS (upper panel) and urine from a patient with MCNS (lower panel). When PBS is used as the elution buffer, suppressive activity migrates with an apparent molecular weight of 110–150,000 daltons, in the two fractions preceding the BSA peak. When pyridine-acetic acid is used, the apparent molecular weight is 10–15,000 daltons for both lymphocyte SIRS and the urine suppressor factor. A shift in apparent molecular weight between the two buffer systems also occurs with murine SIRS, and appears to reflect binding of SIRS to other proteins under certain physiologic conditions as reported by Aune, Webb and Pierce, *J. Immunol.* 131, 2348–52 (1983).

EXAMPLE 3

Screening of urine for SIRS using characteristics of the SIRS pathway. Because of similarities between the migration patterns for SIRS and urine suppressive activity, the urine fractions from the Sephacryl S-200 column chromatography of Example 2, above, which contained suppressive activity were pooled and screened for SIRS activity by using several characteristics of the SIRS pathway. To evaluate the kinetics of suppression and potential activation by peroxide, urine factor was added on day 1 or day 6 to 7-day lymphocyte cultures. In the test shown in Table 2, below, urine factor added early in the culture period suppressed PFC responses by 60 percent. On day 6, addition of urine factor did not cause suppression; however, urine factor reacted with $10^{-8}$M $H_2O_2$ for 20 minutes before addition to culture suppressed responses as well as factor added on day 1. Adding peroxide-treated medium on day 6 did not significantly affect responses.

TABLE 2

Effect of day of addition and reaction with peroxide on urine suppressive activity

| Urine factor added | Day added | PFC/Culture |
|---|---|---|
| None | — | 1,785 |
| Factor, 30 µl | 1 | 720 |
| Factor, 30 µl | 6 | 1,680 |
| Factor$_{ox}$*, 30 µl | 6 | 665 |

*Urine in the test group was treated with $H_2O_2$ at a final concentration of $10^{-6}$ M for 20 min. at 4° C. before addition to culture. Media reacted with $10^{-6}$ M $H_2O_2$ added on day 6 did not affect responses.

Cultures were also tested to determine whether addition of levamisole, catalase, and 2-mercaptoethanol blocked suppression by the urine factor. Table 3, below, shows the results of one such test. Control responses were suppressed by 65 percent by addition of 100 µl of the urine factor on day 1. Addition of 5 µg levamisole on day 1 blocked suppression in cultures containing the urine factor, as did addition of catalase (5000 U) or 2-mercaptoethanol ($10^{-4}$M) on day 3. These reagents alone did not significantly affect responses.

TABLE 3

Effects of inhibitors of SIRS activity on urine-derived suppressor factor activity

| Factor Added* | Inhibitor | PCF/Culture |
|---|---|---|
| None | — | 4,460 |
| 100 µl | — | 1,600 |
| 100 µl | Levamisole, 5 µg/ml, Day 1 | 4,160 |
| 100 µl | Catalase, 5,000 U/ml, Day 3 | 4,000 |
| 100 µl | 2-ME, $10^{-4}$ M, Day 3 | 4,320 |

*In all the above cases, factor (100 µl) was added to cultures on day 1 of a 7-day culture period. Addition of inhibitors alone did not significantly affect control responses.

To determine whether the urine factor was inactivated by acidification to pH 2 or incubation with protease, factor was acidified to pH 4 or pH 2 with HCl, then neutralized after 3 hours at 4° C. Alternatively, urine was incubated with protease, 10 µg/ml for 3 hrs at 4° C. All solutions were filter-sterilized before addition to culture on day 1. In the test shown in Table 4, below, acidification to pH 4 had no effect on suppressive activity, but acidification to pH 2 resulted in a loss of activity. Similarly, the urine factor was inactivated by protease. Thus, the ability of $H_2O_2$ to activate the urine factor to suppress responses when added shortly before culture assay, inhibition of suppression by agents which inhibit SIRS activity, and pH and protease sensitivity of the urine suppressive activity are all identical to those described for human lymphocyte SIRS. Taken together with the apparent mol. wt. of the urine factor in physiologic and high ionic strength buffers, these data strongly support the conclusion that suppressive activity of MCNS urine is due to the presence of SIRS.

TABLE 4

Characteristics of urine suppressor factor*

| Factor Treatment | PFC/Culture |
|---|---|
| Control response (no urine factor) | 9,150 |
| Untreated factor | 4,100 |
| pH 4 | 3,800 |
| pH 2 | 10,750 |
| Protease | 8,300 |

*Urines were treated by adjusting pH to 4 or 2 with HCl, then neutralizing with NaOH after 3 hours at 4° C. Alternatively, urine was incubated with protease, 10 µg/ml, for 3 hr at 0–4° C. before addition to culture.

EXAMPLE 4

Figure 2:
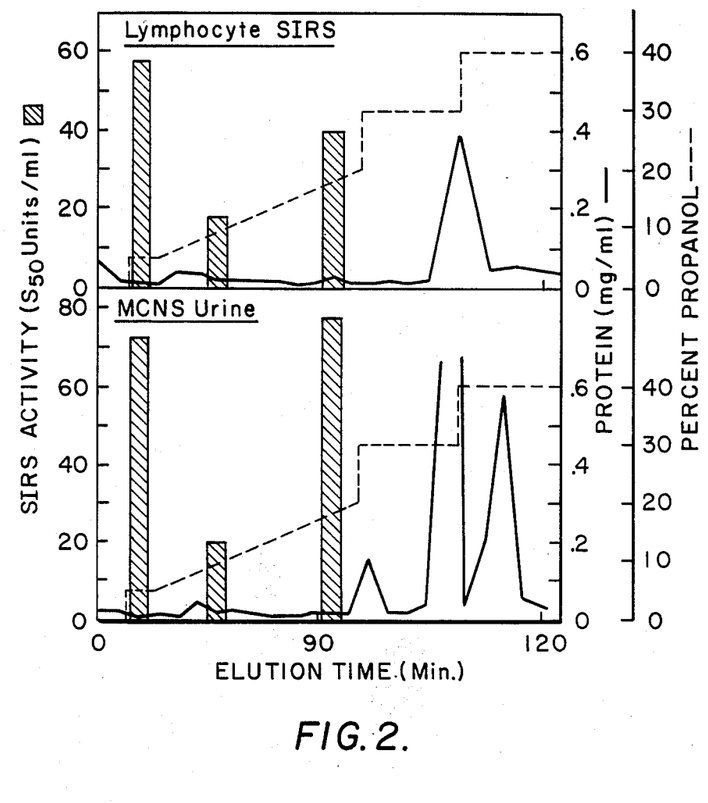
FIG. 2 shows the elution profile of high performance liquid chromatography (HPLC) of lymphocyte SIRS and a urine sample from a MCNS patient. Lyophilized crude lymphocyte SIRS (3 mg) prepared from Concanavalin A-activated human peripheral blood mononuclear cells (upper panel) or 5 mg of lyophilized urine from a patient with MCNS (lower panel) was applied to a Lichrosorb ® RP-8 (10 μM) column equilibrated in 1.0M pyridine, 0.5M acetic acid, pH 5.5, and eluted by reverse phase HPLC using an increasing gradient of n-propanol (broken line). Protein concentration of eluted samples (solid line) was determined by the method of Lowry et al., *J. Biol. Chem.* 193, 265–75 (1951); and SIRS activity (bars) was determined by assay on spleen cell cultures.

Fractionation of urine suppressor factor by HPLC. Urine with suppressive activity and human lymphocyte SIRS obtained from Con A (Concanavalin A) activated PBMC were fractionated by reverse-phase HLPC on an RP-8 (10 µM) analytical column. Protein was eluted by an increasing gradient of n-propanol. FIG. 2 of the accompanying drawings compares the separation of biological activity and protein for lymphocyte SIRS (upper panel) and for urine SIRS (lower panel). In both tests, SIRS activity was separated from the major protein peaks present. Two major SIRS peaks eluted at the 5 percent propanol step-up and at 18 perccent propanol on the linear gradient. A smaller, third peak of SIRS activity eluted at 8 to 9 percent propanol. All of the SIRS bound to the column; none was detected in the initial flow-through during column loading. Further, all activity loaded on the RP-8 column was recovered in the three active peaks; no SIRS activity was eluted by higher propanol concentration or by extended elution times. The identical elution patterns from HPLC supports the conclusion that the urine SIRS and lymphocyte SIRS are similar proteins.

EXAMPLE 5

Use of monoclonal anti-murine SIRS antibodies to absorb urine suppressive activity. Four available monoclonal antibodies to murine SIRS were used in this Example. Lymphocyte SIRS and urine SIRS were incubated with Sepharose beads coupled to each of the anti-murine SIRS antibodies to determine whether suppressive activity was absorbed from the solution. Table 5, below, shows that each antibody removed both human lymphocyte SIRS and urine SIRS from solution. Using similar methods, rat antibodies against an antigen-specific murine suppressor factor (anti-GAT-TsF1, provided by Dr. Craig Sorensen, Washington University School of Medicine), did not absorb activity. These antibodies are described by Sorensen and Pierce, J. of Cellular Biochem., Supp. 8A, 1984, Abstract 0461, p. 169. This pattern of antigenic similarity supports the conclusion that human lymphocyte SIRS is similar to human urine SIRS and also shows that both of these human SIRS proteins are similar to murine SIRS. In the term anti-GAT-TsF1, GAT=random polymer of L-glutamic acid$^a$-L-alanine$^{30}$-L-tyrosine$^{10}$;
GAT-TsF=GAT-specific suppressor T cell factor;
Ts1,TsF1=first order suppressor T cell, single chain TsF.

TABLE 5

Absorption of urine suppressive activity with monoclonal anti-murine SIRS antibody*

| | PFC/Culture | |
|---|---|---|
| | Lymphocyte SIRS 100 µl | Urine SIRS 200 µl |
| Control response | 7600 | |
| Factor | 2,920 | 3,580 |
| +Anti-SIRS$_1$ | 5,520 | 6,180 |
| +Anti-SIRS$_2$ | 6,160 | 6,520 |
| +Anti-SIRS$_3$ | 5,840 | 7,900 |
| +Anti-SIRS$_4$ | 6,000 | 9,300 |
| +AA4.9** | 2,750 | 3,400 |
| +AC4.5** | 2,160 | 3,560 |

*Factor was incubated for 1 hr at 4° C. with monoclonal rat anti-murine SIRS antibody coupled to CNBr-activated Sepharose beads, then filter-sterilized before addition to culture on day 1 of a 7-day culture period.
**Monoclonal rat antibodies directed against murine, GAT-specific suppressor factor.

EXAMPLE 6

Figure 3:
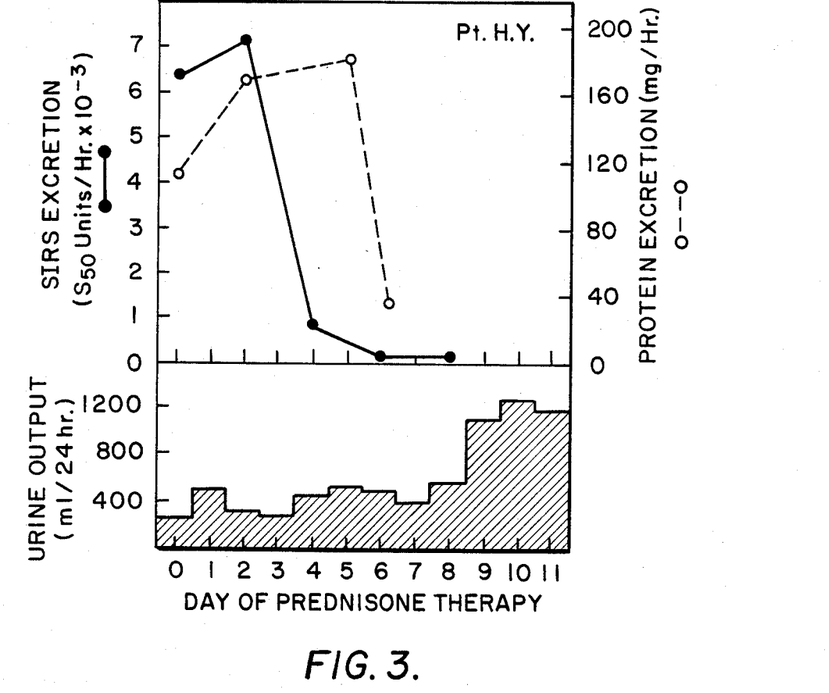
FIG. 3 shows the response in SIRS excretion and urine output of a nephrotic patient undergoing steroid (prednisone) therapy. Serial urine collections were obtained from the patient, (Pt. H.Y.) an 11 year old boy with biopsy-proven MCNS undergoing prednisone therapy. The closed circles indicate urinary SIRS excretion. Protein excretion (open circles) was determined by analysis of urine resuspended in medium using the method of Lowry (protein was not determined on the sample from day 8 because albumin was added to that urine prior to processing). Daily urine output is indicated by the bars on the lower graph.

Disappearance of urine SIRS with treatment of nephrotic syndrome. To determine the relationship of urine SIRS activity to the disease state and treatment, serial urines were collected from patients from the time of initiation of treatment until remission of nephrotic syndrome. FIG. 3 of the accompanying drawings shows the course of a patient (patient 1) undergoing steroid therapy. SIRS activity was present before the beginning of treatment, but disappeared from the patient's urine by the fourth or fifth day of therapy. Although suppressive activity was markedly decreased by day 4, protein excretion remained high, indicating that suppressive activity was not a function of protein excretion. Along with the decrease in proteinuria, onset of diuresis also followed the loss of suppressive activity. Table 6, below, summarizes the results of 5 patients followed in this manner. In all patients, loss of suppressive activity preceded clinical response as indicated by the beginning of a decrease in proteinuria, onset of diuresis and final disappearance of urine protein. This temporal relationship was maintained regardless of whether the patient was studied during an initial presentation with MCNS or relapse, or whether remission occurred rapidly (4–5 days) or more slowly.

TABLE 6

Comparison of urine suppressive activity with clinical response during prednisone treatment of MCNS*

| | SIRS Activity | | Clinical Response | | |
|---|---|---|---|---|---|
| Patient | Last Treatment Day Present | First Treatment Day Absent | Last Day Maximal Urine Protein** | Day of Onset of Diuresis§ | First Day Protein-free Urine** |
| 1 | 2 | 4 | 5 | 9 | 11 |
| 2 | 0 | 3 | 3 | 5 | 14 |
| 3 | 0 | 1 | 1 | 4 | 7 |
| 4 | 1 | 3 | 5 | 6 | 8 |

TABLE 6-continued

Comparison of urine suppressive activity with clinical response during prednisone treatment of MCNS*

| Pa-tient | SIRS Activity | | Clinical Response | | |
|---|---|---|---|---|---|
| | Last Treatment Day Present | First Treatment Day Absent | Last Day Maximal Urine Protein** | Day of Onset of Diuresis§ | First Day Protein-free Urine** |
| 5 | 7 | 12 | 12 | 14 | 16 |

*Patients with known or suspected MCNS were given prednisone, 2 mg/kg orally beginning on day 1. Serial urine collections were obtained and tested for suppressive activity as described in the methods section of the specification preceding Example 1, above. The numbers in the table denote the day of treatment on which each observation was made.
**Urine protein was determined by use of urinalysis dipsticks (Albustix ®, Ames, Elkhart, IN). "Maximal" protein excretion was indicated by a reading of 4+ on all urine specimens. The dipstick scale runs from 1+ to 4+ (minimum to maximum) urine output. Such dipsticks are described, e.g., in U.S. Pat. No. 3,485,587.
§Defined as the first day of sustained, marked increase in urine output.

EXAMPLE 7

Screening of urine from patients with various proteinuric renal disorders. Urine samples from children with proteinuria of various etiologies were screened for suppressive activity on PFC cultures. Each sample was tested at least three times, and the mean number of suppressive units per ml of urine determined for each patient. The results of these assays are summarized in Table 7, below. Patients with steroid-responsive NS or biopsy-proven MCNS constitute the largest group of patients tested. All 11 steroid-responsive patients had suppressive activity, with a mean of 55 and a range of 38-100 units/ml. Mol. wt. of urine SIRS was identical in 6 of 6 of the tested patients and was identical to that of lymphocyte-derived SIRS. SIRS-mediated suppression was confirmed in these 6 samples by activation with peroxide, inhibition by reagents which block SIRS activity, or inactivation by protease or acidification to pH 2. Urine samples from 2 patients with MCNS in remission who were no longer on steroid therapy did not contain SIRS activity. Further, 2 patients who were unresponsive to steroids but had normal glomerular histology on biopsy also did not excrete SIRS.

Two nephrotic patients with Type I membranoproliferative glomerulonephritis showed considerable suppressive activity in their urine, with a mean of 55 units/ml (50 and 60 units, respectively). Suppression from one of these urines was confirmed as SIRS-mediated by all the screening tests listed above, including antibody absorption. After treatment with steroids, both patients became non-nephrotic; in one, steroids have been discontinued. During remmission of nephrosis neither patient excreted SIRS in the urine, although persistent proteinuria and hypocomplementemia indicated that the primary nephritic process was still active.

Urine samples were obtained from four patients with apparent glomerulonephritis. Three of these patients were biopsied because of atypical features which included mild nephrotic syndrome. Two of the biopsied patients (one diagnosed morphologically as having immune complex nephritis, the other, "nephritis with omniglomerular sclerosis") had small amounts of suppressive activity (5 and 17 units/ml, respectively).

Neither of 2 patients with focal glomerulosclerosis had urine SIRS despite massive proteinuria. Urine from 2 non-nephrotic children with systemic lupus erythematosus who were proteinuric did not contain SIRS. One patient each with diabetic nephropathy, congenital nephrosis, and transient proteinuria of undetermined etiology (not nephrotic) also had no urinary SIRS activity.

TABLE 7

Summary of Screening for Urine SIRS Activity*

| Diagnosis | Patients with Urine SIRS Activity Present | Patients with Urine SIRS Activity Absent | Mean $S_{50}$ units per ml in positive urines |
|---|---|---|---|
| MCNS, steroid responsive | | | |
| active disease | 11 | 0 | 55 |
| remission | 0 | 2 | — |
| MCNS, steroid unresponsive | 0 | 2 | — |
| Membranoproliferative Glomerulonephritis | | | |
| nephrotic | 2 | 0 | 55 |
| not nephrotic | 0 | 2 | — |
| Acute Glomerulonephritis | 2 | 2 | 11 |
| Focal Glomerulosclerosis | 0 | 2 | — |
| Systemic Lupus Erythematosus not nephrotic | 0 | 2 | — |
| Other Proteinuria** | 0 | 3 | — |

*Each patient sample was screened at least 3 times, each time on cultures of different lymphocytes, for suppressive activity. The mean number of $S_{50}$ units/ml was determined for each sample.
**One patient each with diabetic nephropathy, congenital nephrosis, and transient proteinuria of undetermined etiology.

In the foregoing examples, it will be seen that in order to determine whether SIRS was produced by patients with NS, urines of MCNS patients were evaluated for ability to suppress PFC responses. Suppressive activity was found in urines from all patients with SRNS in relapse. Table 8, below, summarizes characterization of this suppressive activity and compares the urine factor to human lymphocyte SIRS. The two factors have similar migration patterns on gel filtration with physiologic and high ionic strength buffers. HPLC of each factor is identical, yielding 2 larger peaks accounting for about 80 percent of total activity at 5 percent and 18 percent propanol, and a smmall peak at 8-9 percent propanol. Both factors must be added near the time of culture initiation to suppress responses but when activated by reaction with $H_2O_2$ can cause suppression when added late in the culture period. Catalase and levamisole, which block activation of SIRS, and 2-mercaptoethanol, which inactivates $SIRS_{ox}$, each inhibit urine suppressor factor activity. Both lymphocyte SIRS and urine SIRS were acid-labile and inactivated by protease. Finally, monoclonal anti-murine SIRS antibodies absorbed both human lymphocyte and urine-derived SIRS activity from solution. These findings clearly demonstrate that SIRS, which has been characterized previously by in vitro techniques, is produced in vivo and is related to the disease state in certain patients.

TABLE 8

Comparison of human lymphocyte and urine SIRS

| | Lymphocyte SIRS | MCNS Urine SIRS |
|---|---|---|
| Molecular Weight | | |
| PBS | 110-150,000 | 110-150,000 |
| Pyr-HAc | 10-15,000 | 10-15,000 |
| HPLC | | |
| Peak 1 | 5 percent propanol | 5 percent propanol |
| Peak 2 | 8-9 percent propanol | 8-9 percent propanol |
| Peak 3 | 18 percent propanol | 18 percent propanol |
| Optimal time of | Day 1 | Day 1 |

TABLE 8-continued

Comparison of human lymphocyte and urine SIRS

| | Lymphocyte SIRS | MCNS Urine SIRS |
|---|---|---|
| addition | | |
| Activation by peroxide | + | + |
| Inhibition by catalase and levamisole | + | + |
| Inhibition by 2-ME | + | + |
| Acid Lability | pH 2 | pH 2 |
| Inactivation by protease | + | + |
| Absorption of activity by anti-murine SIRS antibodies | + | + |

2-ME = mercaptoethanol

In order to further demonstrate the production of SIRS from urine, a resuspended lyophilized urine sample from a nephrotic patient was subjected to ammonium sulfate salt fractionation followed by chromatofocusing of the resuspended protein fraction.

The ammonium sulfate salt fractionation separates proteins by stepwise precipitation at varying percent of saturation. The desired protein precipitate fraction is then resuspended in phosphate buffered saline (PBS) and subjected to chromatofocusing.

Chromatofocusing is a high resolving chromatographic method which separates proteins according to their isoelectric point. Proteins are eluted as sharply focused, well separated zones in a linear pH gradient. In chromatofocusing, the proteins, after initially binding at the top of the column to a Polybuffer Exchange resin, migrate down as the pH gradient develops. The rate of movement of a particular level in the pH gradient down the column is lower than the rate of flow of the Polybuffer. Trailing proteins are carried quickly downward and catch up with the region where they bind to the column and, thereby, maintain a narrow zone width.

Further background information on chromatofocusing can be had by reference to *Chromatofocusing with Polybuffer ® and PBE ®*, Pharmacia Fine Chemicals AB, Uppsala, Sweden, 1982; Richey and Beadling, *Amer. Lab.* 13, October 1981, pp. 100-2, 107-10; and Sluyterman, *Trends in Biochem. Sci.* 7, 168-70 (1982).

Table 9, below, shows the results of isolation of SIRS activity from the urine in a nephrotic patient with ammonium sulfate salt fractionation at 15%-50% saturation followed by chromatofocusing. SIRS activity was reported in $S_{50}$ units as defined hereinbefore.

TABLE 9

Fractionation of urine suppressor factor by $(NH_4)_2SO_4$ precipitation and chromatofocusing

| Condition | Total Units of SIRS Activity | Protein milligrams | Units Per mg Protein | Purification Factor |
|---|---|---|---|---|
| Lyophilized Urine | $4 \times 10^4$ | 500 | 80 | — |
| Ammonium Sulfate Fraction* | $4 \times 10^4$ | 22 | 1800 | 23 |
| Chromatofocusing** | $3.8 \times 10^4$ | 0.35 | $1.1 \times 10^5$ | $1.4 \times 10^3$ |

*Urine was resuspended in PBS, and ammonium sulfate was added to a final concentration of 15% saturation. After removal of the precipitate by centrifugation, ammonium sulfate was added to the supernatant to reach 50% saturation. After centrifugation, the supernatant was discarded and the resulting precipitate was resuspended in PBS and dialyzed against PBS before testing for SIRS activity.
**The resuspended fraction from the ammonium sulfate salt fractionation was applied to a PBE 94 (Polybuffer Exchange, Pharmacia Fine Chemicals) chromatofocusing column equilibrated to pH 8.3 with 0.025 M Tris buffer and eluted with Polybuffer 96/Polybuffer 74 (Pharmacia Fine Chemicals), pH 5.0, thereby creating a pH gradient from 8.3 to 5.0. SIRS activity eluted in a single peak at pH 6.8.

Various other examples and modifications of the foregoing examples will be apparent to the person skilled in the art after reading the present disclosure without departing from the spirit and scope of the invention and it is intended that all such further examples and modifications be included within the scope of the appended claims.

What is claimed is:

1. An in vitro diagnostic method of screening for immune deficiency in a nephrotic patient comprising determining the presence or absence of the lymphokine, soluble immune response suppressor (SIRS), in a urine sammple of said patient by detecting physical, chemical or functional characteristics of SIRS and comparing said characteristics with known control values of SIRS.

2. The method of claim 1 in which said characteristics are the elution pattern on high performance liquid chromatography.

3. The method of claim 1 in which said detection of sample SIRS consists of activation and inhibition, in which said activation comprises activation by peroxide to $SIRS_{ox}$ and said inhibition comprises inhibition of suppression by reagent selected from the group consisting essentially of catalase, levamisole and 2-mercaptoethanol.

4. The method of claim 1 in which said characteristics are the cross-reactivity with monoclonal rat anti-murine SIRS antibodies coupled to agarose beads.

* * * * *

UNITED STATES PATENT AND TRADEMARK OFFICE
CERTIFICATE OF CORRECTION

PATENT NO. : 4,665,021

DATED : May 12, 1987

INVENTOR(S) : H. WILLIAM SCHNAPER and THOMAS M. AUNE

It is certified that error appears in the above—identified patent and that said Letters Patent is hereby corrected as shown below:

In the Abstract, line 3, "administering" should read --determining--.

In col. 10, line 8 "L-glutamic acid$^{\alpha}$" should read --L-glutamic acid$^{60}$--.

Signed and Sealed this

First Day of September, 1987

Attest:

DONALD J. QUIGG

Attesting Officer

Commissioner of Patents and Trademarks